US00PP34283P2

(12) United States Plant Patent
Snijder

(10) Patent No.: US PP34,283 P2
(45) Date of Patent: May 31, 2022

(54) ***PELARGONIUM* PLANT NAMED 'PECZ0025'**

(50) Latin Name: ***Pelargonium* x *hortorum***
Varietal Denomination: PECZ0025

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/300,461

(22) Filed: Jul. 6, 2021

(51) Int. Cl.
*A01H 5/02* (2018.01)
*A01H 6/42* (2018.01)

(52) U.S. Cl.
USPC ..... Plt./327
CPC ..... *A01H 6/425* (2018.05)

(58) Field of Classification Search
USPC ..... Plt./327
CPC ..... A01H 6/425
See application file for complete search history.

(56) References Cited

PUBLICATIONS

UPOV hit on *Pelargonium* plant named, 'PECZ0025', QZ PBR 2021/1597, filed Jun. 14, 2021.*
CPVO application on *Pelargonium* plant named, 'PECZ0025'QZ PBR 2021/1597, filed Jun. 14, 2021.*
CPVO Application Consultation of a UPOV hit on a *Pelargonium* plant named, 'PECZ0025', QZ PBR 2021/1597, filed Jun. 14, 2021.*

* cited by examiner

*Primary Examiner* — Anne Marie Grunberg
(74) *Attorney, Agent, or Firm* — Dale Skalla

(57) ABSTRACT

A new *Pelargonium* plant named 'PECZ0025' particularly distinguished by salmon-rose colored inflorescences with single florets, held above yellow-green foliage with large brown zoning, on a vigorous plant.

1 Drawing Sheet

Latin name of the genus and species of the plant claimed: *Pelargonium* x *hortorum*.
Varietal denomination: 'PECZ0025'.

BACKGROUND OF THE NEW PLANT

The present invention comprises a new *Pelargonium*, botanically known as *Pelargonium* x *hortorum*, and hereinafter referred to by the variety name 'PECZ0025'.

'PECZ0025' is a product of a planned breeding program. The new cultivar 'PECZ0025' has salmon-rose colored inflorescences with single florets, held above yellow-green foliage with large brown zoning, on a vigorous plant.

'PECZ0025' originates from a hybridization in a controlled breeding program made in July 2007, in a greenhouse in Hillscheid, Germany. The female parent was an unpatented plant of *P.* x *hortorum* parentage identified as 'Indian Dunes' with orange red pigmented florets, when compared to 'PECZ0025'.

The male parent of 'PECZ0025' was a patented, proprietary plant of *P.* x *hortorum* parentage, identified as 'Grawit', described in U.S. Plant Pat. No. 18,773 with a denser plant habit and lesser pigmented flower petals when compared to 'PECZ0025'. The resultant seed was sown in January 2008.

'PECZ0025' was selected as one flowering plant within the progeny of the stated cross in May 2008 in a greenhouse in Hillscheid, Germany.

The first act of asexual reproduction of 'PECZ0025' was accomplished when vegetative cuttings were propagated from the initial selection in June 2008 in a greenhouse in Hillscheid, Germany.

BRIEF SUMMARY OF INVENTION

Horticultural examination of plants grown from cuttings of the plant initiated in May 2009 in Enkhuizen, The Netherlands and continuing thereafter, has demonstrated that the combination of characteristics as herein disclosed for 'PECZ0025' are firmly fixed and are retained through successive generations of asexual reproduction.

'PECZ0025' has not been observed under all possible environmental conditions. The phenotype may vary significantly with variations in environment such as temperature, light intensity, and day length.

A Plant Breeder's Right for this cultivar was applied for in the European Union on Jun. 14, 2021, No. 2021/1597. 'PECZ0025' has not been made publicly available prior to the effective filing date of this application, notwithstanding any disclosure that may have been made less than one year prior to the effective filing date of this application by the inventor or another who obtained 'PECZ0025' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
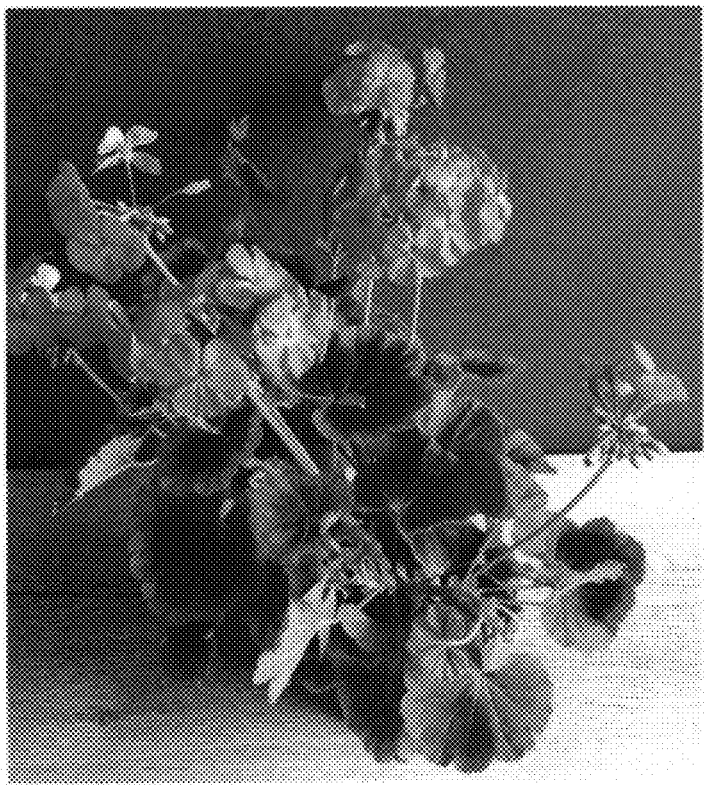
Figure 2:
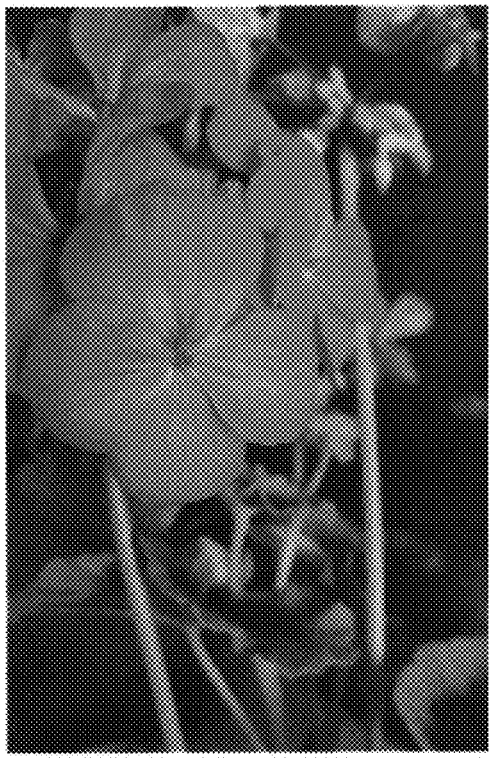

The accompanying photographic drawings show typical flower and foliage characteristics of 'PECZ0025' with colors being as true as possible with an illustration of this type. The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in early June 2021 under natural light. These plants were approximately 16 weeks old and were grown in a 12 cm pots, in a greenhouse trial. The plants shown in the photographs were about 16 weeks old growing in a 12 cm pot in a greenhouse. The photographs were taken in June 2021.

Color references are made to The Royal Horticultural Society Colour Chart (R.H.S.) 2001.

TABLE 1

DIFFERENCES BETWEEN THE NEW VARIETY 'PECZ0025' AND A MOST SIMILAR VARIETY

| | 'PECZ0025' | 'Fipelbrofir' (U.S. Plant Pat. No. 29,015) |
|---|---|---|
| Color of upper surface of upper petal: | Salmon rose - between RHS 63C and RHS 50B | Orange red - close to RHS 43B |
| Number of petals per flower: | Five | Five-seven |

Plant:
- *Form, growth and habit*.—Mounding, Semi-spreading.
- *Plant height*.—17-19 cm.
- *Plant height (inflorescence included)*.—28-32 cm.
- *Plant width*.—33-38 cm.

Roots:
- *Number of days to initiate roots*.—15-18 days at about 22 degrees C.
- *Number of days to produce a rooted cutting*.—21-23 days at 22 degrees C.
- *Type*.—Fine, fibrous, free branching.
- *Color*.—RHS N155B but whiter.

Foliage:
- *Variegation*.—Absent.
- *Immature leaf, color upper surface*.—Closest to RHS 143C.
- *Immature leaf, lower surface*.—Closest to RHS 138B.
- *Mature leaf, color upper surface*.—Closest to RHS 143A.
- *Mature leaf, color lower surface*.—Closest to RHS 139C.
- *Length*.—7-9 cm.
- *Width*.—8-11 cm.
- *Shape*.—Cordate.
- *Base shape*.—Cordate.
- *Sinus of mature leaf*.—Very narrow.
- *Leaf base openness*.—Open or slightly open, seldom closed.
- *Apex shape*.—Rounded.
- *Margin*.—Slightly dentate.
- *Texture upper side*.—Hirsute.
- *Texture lower side*.—Hirsute.
- *Leaf zonation color*.—RHS 177A.
- *Leaf zonation width*.—6-8 cm.
- *Leaf zonation length*.—7-10 cm.
- *Color of veins, upper surface*.—RHS 143A.
- *Color of veins, lower surface*.—RHS 138B, largely indistinct.
- *Pattern of veining*.—Palmate.
- *Petiole color*.—RHS 143C.
- *Petiole length*.—5-6 cm.
- *Diameter of petiole*.—0.25 cm.
- *Texture*.—Pilose, hirsute, glandular hairs.

Stem:
- *Quantity of branches*.—5-9.
- *Color of stem*.—RHS 143C.
- *Anthocyanin coloration of stem*.—A weak anthocyanin coloration is visible under solar radiation.
- *Length of stem*.—9-17 cm.
- *Diameter*.—0.5 cm.
- *Length of internodes*.—1-6 cm.
- *Texture*.—Sparsely hirsute, pilose, glandular hairs.

Peduncle:
- *Color of peduncle*.—RHS 144A.
- *Length of peduncle*.—12-18 cm.
- *Peduncle diameter*.—0.3-0.4 cm.
- *Texture*.—Hirsute, glandular hairs.
- *Anthocyanin coloration of peduncle*.—A slight anthocyanin coloration is visible under high solar radiation on middle third.

Pedicel:
- *Color of pedicel*.—Mature RHS 181B; immature RHS N144C.
- *Length of pedicel*.—1.5-3 cm.
- *Diameter of pedicel*.—0.15-0.2 cm.
- *Texture*.—Sparsely pilose, glandular hairs.
- *Pedicel swelling*.—Swelling was not observed.

Bud (just before opening):
- *Color*.—RHS 62A.
- *Length*.—1.1-1.2 cm.
- *Width*.—0.5 cm.
- *Shape*.—Elliptical.

Inflorescence:
- *Type*.—Umbel; semi-spherical or nearly semi-spherical.
- *Lastingness of individual flowers*.—7-9 days at 18° C. temperature.
- *Number of inflorescences per plant*.—6-12, with 5-12 immature umbels in various stages.
- *Average total number of buds*.—36-45.
- *Fragrance*.—None.
- *Umbel diameter*.—8-9 cm.
- *Umbel depth*.—5-7 cm.

Corolla:
- *Form*.—Single.
- *Number of petals*.—5.
- *Diameter of flower*.—3.4-3.8 cm.
- *Depth of flower*.—0.9-1.2 cm.
- *Side view shape*.—Concave.
- *Color upper petals, upper surface*.—RHS 63C at anthesis, fading to RHS 50B at the edge, veins RHS 52A.
- *Color upper petals, lower surface*.—RHS 62B, veins RHS N57B.
- *Length of upper petals*.—1.4-1.9 cm.
- *Width of upper petals*.—1.3-1.4 cm.
- *Color lower petals, upper surface*.—RHS 43B fading with age to RHS 47C.
- *Color lower petals, lower surface*.—RHS 62C, mottled RHS 50C.
- *Markings on upper petals*.—Veins RHS 52A.
- *Markings on lower petals*.—None.
- *Length of lower petals*.—1.5-1.7 cm.

*Width of lower petals.*—1.5-1.6 cm.
*Petal shape*.—Obovate to spathulate.
*Apex shape*.—Rounded.
*Margin*.—Entire.
*Base*.—Attenuate.
*Petal texture*.—Papillose on both surfaces.

Calyx:
*Number of sepals*.—5.
*Color of sepals*.—RHS N144A.
*Length of sepals.*—0.8-0.9 cm.
*Width of sepals.*—0.2-0.4 cm.
*Sepal shape*.—Lanceolate to linear.
*Apex shape*.—Acute.
*Margins*.—Mostly fused.
*Texture, upper surface*.—Glabrous.
*Lower surface*.—Glandular hairs, hirsute.
*Sepal flexing*.—Sepals flexed in mature florets. Upper sepal never flexed.

Reproductive organs:
Gynoecium:
*Pistil*.—RHS 55A.
*Length*.—0.5-0.6 cm.
*Style color*.—RHS 55A.
*Style length*.—0.3 cm.
*Stigma color*.—Immature RHS 51A; mature RHS 55A.
*Ovary color*.—RHS 144B.
*Ovary length*.—0.3 cm.
*Ovary diameter*.—0.2 cm.

Androecium:
*Number of stamens*.—5.
*Color of filaments*.—RHS N157B, tip RHS 51A.
*Length filaments*.—0.4-0.5 cm.
*Anther color*.—RHS 51B.
*Length of anthers*.—0.2 cm.
*Color of pollen*.—RHS 31A.
*Pollen amount*.—Abundant.
*Fertility/seed set*.—Has not been determined to date.
*Disease/pest resistance*.—Has not been determined to date.

What is claimed is:

1. A new and distinct variety of *Pelargonium* plant named 'PECZ0025' substantially as illustrated and described herein.

* * * * *